US008530689B2

(12) United States Patent
Percec et al.

(10) Patent No.: US 8,530,689 B2
(45) Date of Patent: Sep. 10, 2013

(54) PROCESSES FOR THE PREPARATION OF BIPHENYL COMPOUNDS

(75) Inventors: Virgil Percec, Philadelphia, PA (US); Brad Matthew Rosen, Philadelphia, PA (US); Daniela A. Wilson, Rotherham (GB); Christopher J. Wilson, Rotherham (GB)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/991,011

(22) PCT Filed: Apr. 30, 2009

(86) PCT No.: PCT/US2009/042243
§ 371 (c)(1),
(2), (4) Date: Feb. 8, 2011

(87) PCT Pub. No.: WO2009/137322
PCT Pub. Date: Nov. 12, 2009

(65) Prior Publication Data
US 2011/0207957 A1    Aug. 25, 2011

Related U.S. Application Data

(60) Provisional application No. 61/050,410, filed on May 5, 2008, provisional application No. 61/096,991, filed on Sep. 15, 2008.

(51) Int. Cl.
C07F 5/04 (2006.01)
C07C 67/343 (2006.01)
C07C 41/30 (2006.01)

(52) U.S. Cl.
USPC ............ 558/288; 558/298; 560/59; 560/102; 568/6; 568/642; 568/643

(58) Field of Classification Search
None
See application file for complete search history.

(56) References Cited

U.S. PATENT DOCUMENTS
7,122,694 B2    10/2006  Marcuccio et al.

OTHER PUBLICATIONS

Kikuchi et al., "Practical Synthesis of Pinacolborane for One-Pot Synthesis of Unsymmetrical Biaryls via C-H Borylation-Cross-Coupling Sequence", Tetrahedron, May 26, 2008, 64(22), 4967-4971.
Saito et al., "Synthesis of Biaryls via a Nickel(0)-Catalyzed Cross-Coupling Reaction of Chloroarenes with Arylboronic Acids", J. Org. Chemistry, May 2, 1997, 62(23), 8024-8030.

*Primary Examiner* — Joseph K. McKane
*Assistant Examiner* — Amanda L Aguirre
(74) *Attorney, Agent, or Firm* — Woodcock Washburn, LLP

(57) ABSTRACT

The invention concerns processes for the synthesis of a compound of the formula: wherein: $R^1$ and $R^2$ are each, independently, $C_1$-$C_{12}$ alkyl, $CO_2R^3$, $OR^4$, $R^5(OR^6)$, or $C_6$-$C_{18}$ aryl; $R^3$-$R^6$ are each, independently, $C_1$-$C_{12}$ alkyl or $C_6$-$C_{12}$ aryl; and n and m are each, independently, 0 or an integer from 1-5; said process comprising:—contacting a compound of the formula $HO$-$R^7$-$OH$ with $BH_3$ and a compound of the formula in the presence of a nickel-containing catalyst to produce a first product, where $R^7$ is a $C_2$-$C_{12}$ hydrocarbon group and X is a halogen, OMs or OTs;—contacting the first product in situ with a compound of the formula: in the presence of a nickel-containing catalyst to produce a compound of formula I, where Z is a halogen.

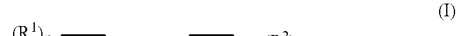

(I)

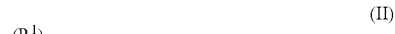

(II)

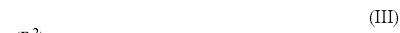

(III)

11 Claims, 1 Drawing Sheet

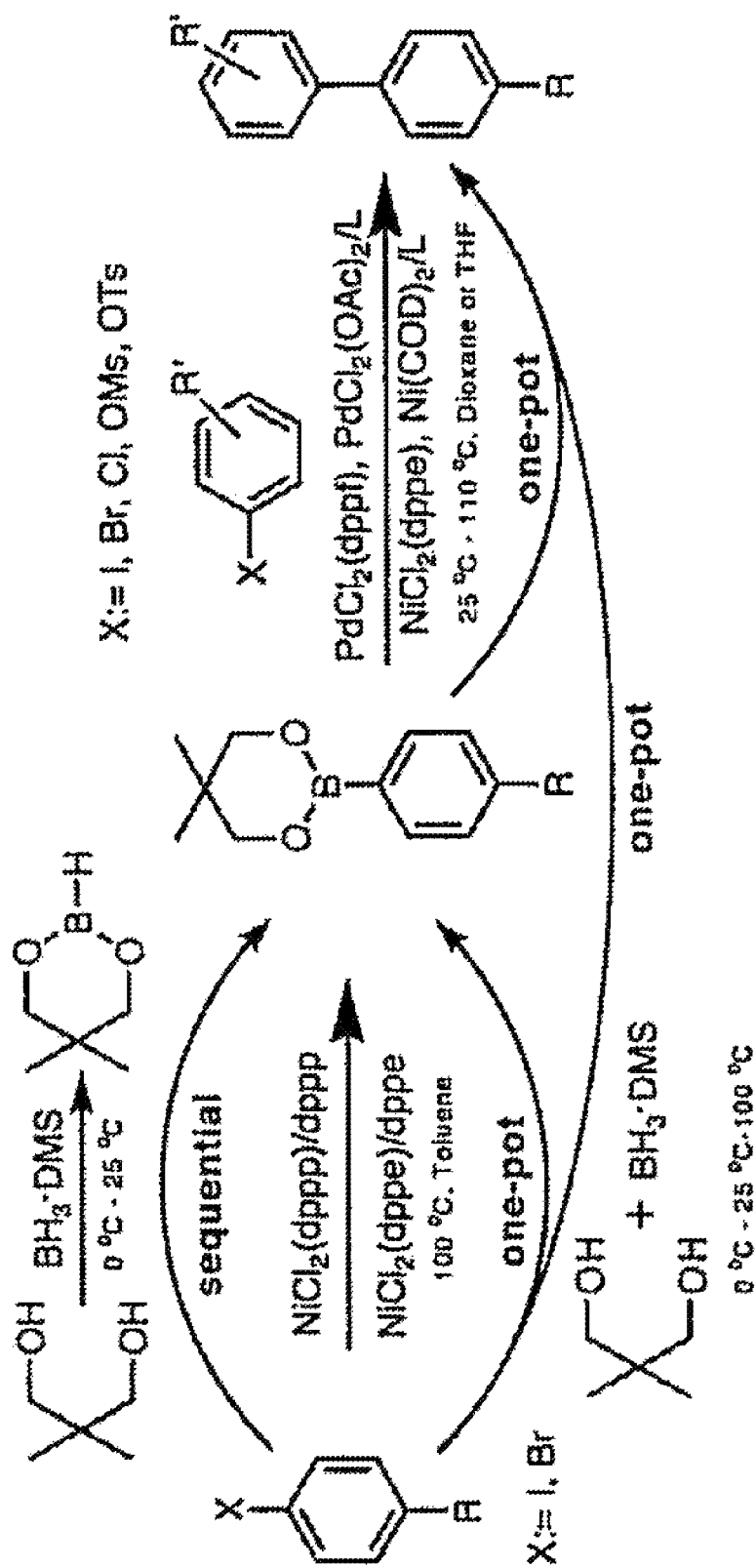

PROCESSES FOR THE PREPARATION OF BIPHENYL COMPOUNDS

CROSS-REFERENCE TO RELATED APPLICATIONS

This application is the National Stage of International Application No. PCT/US2009/042243, filed Apr. 30, 2009, which claims the benefit of U.S. Provisional Application No. 61/050,410, filed May 5, 2008 and U.S. Provisional Application No. 61/096,991, the disclosures of which are incorporated herein by reference in their entireties.

STATEMENT OF GOVERNMENT RIGHTS

The invention was made with U.S. Government support. The Government may have certain rights in the invention through the National Science Foundation under federal grant number NSF DMR-0548559.

TECHNICAL FIELD

The present invention concerns processes for the production of aryl neopentylglycolborate esters and their use in the production of biphenyl compounds.

BACKGROUND

Boronic acids are used as intermediates in the synthesis of biaryl and related architectures (Hall, D. G. Ed. Boronic Acids, Wiley-VCH: Weinheim, Germany, 2005), as building blocks for supramolecular polymers (Niu, et al., J. Chem. Commun. 2005, 4342), chemical sensors (James and Shinkai, Top. Curr. Chem. 2002, 218, 159) and therapeutics. The broad applicability of boronic acids in organic synthesis has encouraged pursuit of efficient methods for their synthesis. The traditional approach to arylboronic acids involves the formation of aryl Grignard and lithium reagents, followed by electrophillic trapping with trialkyl borates and subsequent hydrolysis. As it employs the least expensive reagents, this method is one of the few procedures that is used for large-scale applications. The sensitivity of this reaction to moisture and the incompatibility of Grignard and organolithium reagents with electrophillic functional groups are obstacles to its implementation. One solution to this problem is the "in-situ" quench technique, wherein an alkyl lithium reagent is added directly to a solution of aryl halide and trialkyl borate. While this is an improvement, yields are still inadequate for many substrates including carboxylic esters (Li, et al., J. Org. Chem. 2002, 67, 5394). An attractive alternative to direct boronic acid synthesis involves transition metal catalyzed installation of a cyclic boronate ester. The most well known method utilizes Pd(O) (Ishiyama, et al, J. Org. Chem. 1995, 60, 7508; Murata, et al., J. Org. Chem. 1997, 62, 6458) to catalyze the addition of tetraalkoxydiboron (Ishiyama, et al, J. Org. Chem. 1995, 60, 7508; Brotherton, et al., J. Am. Chem. Soc. 1960, 82, 6242; Lawlor, et al., Inorg. Chem. 1998, 37, 5282; Ishiyama, et al., J. Ed. Org. Synth. 2000, 77, 176), pinacolborane (HBPin) (Murata, et al., J. Org. Chem. 1997, 62, 6458; Tucker, et al., J. Org. Chem. 1992, 57, 3482) or catecholborane (Murata, et al., J. Org. Chem. 2000, 65, 164) to an aryl iodide, bromide or triflate. A one-pot Ir catalyzed direct C—H boration was developed to synthesize the relatively inaccessible 3,5-disubstiuted aryl boronic acids and aryltrifluoroborates from 1,3-disubstituted arenes Pd-catalyzed borations of aryl halides and direct Ir catalyzed C—H borations are restrictively expensive due to the cost or extremely difficult synthesis and purification of alkoxydiborons and catalysts (Brotherton, et al., J. Am. Chem. Soc. 1960, 82, 6242; Lawlor, et al., Inorg. Chem. 1998, 37, 5282; Ishiyama, et al., J. Ed. Org. Synth. 2000, 77, 176).

Despite the aforementioned research, there is a need in the art for a simplified, low cost method for the production of biaryl compounds and their boron containing precursors.

SUMMARY

The present invention concerns processes for the production of biphenyl compositions. In some embodiments, the process is for the synthesis of a compound of the formula:

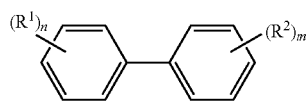

I wherein:
$R^1$ and $R^2$ are each, independently, $C_1$-$C_{12}$ alkyl, $CO_2R^3$, $OR^4$, $R^5(OR^6)$, or $C_6$-$C_{18}$ aryl;
$R^3$-$R^6$ are each, independently, $C_1$-$C_{12}$ alkyl or $C_6$-$C_{12}$ aryl; and
n and m are each, independently, 0 or an integer from 1-5;
the process comprising:
reacting a compound of the formula HO—$R^7$—OH with $BH_3$ and a compound of the formula

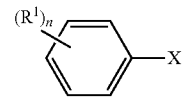

in the presence of a nickel-containing catalyst to produce a first product, where $R^7$ is a $C_2$-$C_{12}$ hydrocarbon group and X is a halogen, OMs, or MTs;
contacting the first product with a compound of the formula:

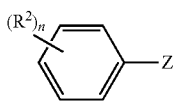

III in the presence of a nickel-containing catalyst to produce a compound of formula I, where Z is a halogen.

In some processes, the compound of the formula HO—$R^7$—OH is contacted with $BH_3$ to produce an intermediate compound prior to contacting said intermediate compound with a compound of formula II. In certain processes, the intermediate is not isolated.

In some embodiments, the nickel-containing catalyst is $NiCl_2$(dppp) in the reacting step (borylation). In certain embodiments, $NiCl_2$(dppe) is used as the nickel-containing catalyst in the contacting step (coupling). In yet other embodiments, $NI(COD)_2/PCy_3$ is used in the reacting step. As the first product can be reacted in situ to produce the compound of formula I, the substantially the same catalyst can be used in each reaction step.

Any suitable solvent can be used in the process. In some embodiments, the compound of formula I is prepared in the presence of toluene solvent.

For some compounds produced by the process, n and m are each, independently, 1 or 2. Some compounds, have n at least one of $R^1$ and $R^2$ is $CO_2R^3$ where $R^3$ is methyl or ethyl. In certain processes, $R^3$ is methyl. In some processes, $R^1$ and $R^2$ are each, independently, $C_1$-$C_4$ alkyl, $CO_2R^3$, $OR^4$, or $C_6$-$C_{18}$ aryl; and $R^3$-$R^6$ are each, independently, $C_1$-$C_4$ alkyl or $C_6$-$C_{12}$ aryl. One preferred X is Br.

In certain embodiments, the first product is of the formula

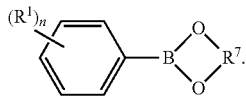
IV

In some embodiments, the invention concerns the process for the production of a compound of the formula:

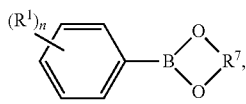
IV the process comprising contacting a compound of the formula HO—$R^7$—OH with $BH_3$ and a compound of the formula

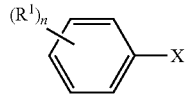
II in the presence of a nickel-containing catalyst to produce a first product,
wherein:
$R^1$ is $C_1$-$C_{12}$ alkyl, $CO_2R^3$, $OR^4$, $R^5(OR^6)$, or $C_6$-$C_{18}$ aryl;
$R^3$-$R^6$ are each, independently, $C_1$-$C_{12}$ alkyl or $C_6$-$C_{12}$ aryl; and
$R^7$ is a $C_2$-$C_{12}$ hydrocarbon group and X is a halogen.

In some embodiments, the compound of formula IV is isolated and optionally purified.

In some embodiments, the reacting and contacting steps are performed seriatim. By performed seriatim, it is intended to mean that the intermediate products are not isolated between reaction steps. Thus, compound I can be produced without isolation of the first product.

In some embodiments, HO—$R^7$—OH and $BH_3$ can be reacted to produce a compound of the formula V.

V

In certain embodiments, compound V can be reacted with compound II to produce compound IV. Compound IV can be reacted with compound III to produce compound I. In some embodiments, compounds IV and V can be reacted to produce compound I without isolation and/or purification of the compounds.

BRIEF DESCRIPTION OF THE DRAWINGS

FIG. 1 presents a schematic of certain sequential and one-pot synthetic processes described herein.

DETAILED DESCRIPTION OF ILLUSTRATIVE EMBODIMENTS

The present invention concerns sequential Ni-catalyzed borylation and cross-coupling of aryl halides via in situ prepared cyclic dialkoxy borane compounds, such as neopentylglycolborane.

In some embodiments, a compound of the formula HO—$R^7$—OH (pinacol, neopentylglycol, or other diols, for example) is contacted with $BH_3$ and results in the formation of a cyclic borane. This compound is produced in situ only, and is not isolated. Contacting the cyclic borane derived in situ via contact with the diol and $BH_3$, with a compound of the formula II and nickel catalyst produces compound IV, a cyclic boronate ester. Compound IV can be isolated and purified. Compounds of formula IV are important commercial products and currently very expensive due to current synthetic methods. In certain embodiments, the compound IV can be contacted with compound III and nickel catalyst to form Compound I, a biphenyl.

One key advantage to the presently described process is the ability to use cheap Ni-catalysts for both the formation of compounds of the formulas IV and I. Importantly, the ability to use unpurified cyclic borane made in situ from the contact of $BH_3$ and HO—$R^7$—OH, for the reaction to produce IV is a significant improvement over previous known methodologies, as it bypasses the purchase of costly borylating reagents or tedious purification of the cylcic borane.

In one embodiment, the invention is depicted in following reaction scheme.

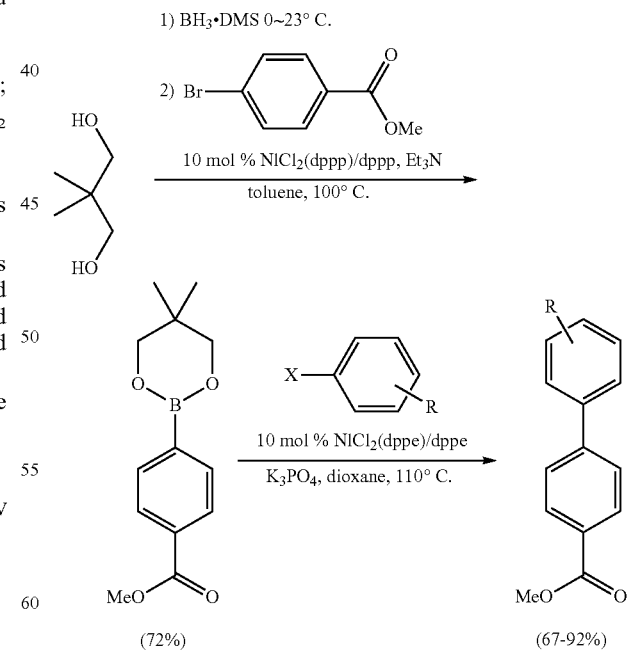

Certain work in our laboratory has focused on the development of Ni-catalysts for Suzuki-Miyaura cross-coupling of aryl halides, tosylates and mesylates (Percec, et al., J. Org. Chem. 1995, 60, 1060; Percec, et al., J. Org. Chem. 2004, 69, 3447). The broad applicability of NiCl$_2$(dppe) for Suzuki-Miyaura cross-coupling and the need for large quantities of boronic acid derived biaryl (Percec, et al, Chem. Eur. J. 2006, 12, 5731) triggered the pursuit of a general method for Ni-catalyzed dialkoxyborations. Ni-catalyzed pinacolborylation has been reported once in the literature (Percec, et al, Chem. Eur. J. 2006, 12, 5731). Therein, the Pd borylation was modified to use less expensive Ni and HBpin for the bis- and trisborylation. For the purpose of multi-borylation, 10% NiCl$_2$(dppp), 1.5 equiv of HBPin per halide, and 3.0 equiv Et$_3$N were suitable (Morgan, et al, J. Appl. Polym. Sci. 2000, 76, 1257). Our investigation into Ni-catalyzed mono-borations used these conditions as a starting point. Two significant modifications were incorporated at the onset of this study. To reduce the cost and eliminate a synthetic step, HBpin was prepared "in situ" by addition of BH$_3$-DMS to a toluene solution of pinacol and directly used in the boration via cannulation without purification. While the use of unpurified HBpin has been reported for hydroborations, prior distillation is standard for metal-catalyzed coupling. To ensure high conversion while using in situ formed HBpin, the starting equiv of HBPin were increased from 1.5 to 2.0. Optimizations of the initial conditions were performed on electron-rich 4-bromoanisole and later on electron deficient methyl 4-bromobenzoate (Table 1). One motivation for the two-substrate optimization is that limited protiodeboration was observed in electron rich substrates, whereas extensive protiodeboration was initially observed in electron poor substrates.

In an initial screen with 4-bromoanisole, it was revealed that solvent choice can be important. Pinacolborylation proceeds in toluene, but did not proceed in dioxane. This is unusual considering that Ni-catalyzed Suzuki-Miyaura cross-coupling proceeds in both dioxane and toluene (Percec, et al., J. Org. Chem. 1995, 60, 1060; Percec, et al., J. Org. Chem. 2004, 69, 3447). Further, dioxane is an acceptable solvent for Pd-catalyzed Miyaura boration using HBpin.

In Pd-catalyzed coupling of dialkoxyboranes with aryl halides, Et$_3$N has been shown to be more efficient than Py, DBU, KOAc, or even Hunig's base. Due to the superiority of Et$_3$N in Pd-catalyzed reactions and the likely similar mechanism for Ni, Et$_3$N was used without investigating other bases. In order to develop the simplest procedure possible, the purity requirements for each reagent were investigated. It was found that the reaction was highly dependent on the quality of Et$_3$N. Use of as received Et$_3$N resulted in 66% conversion after 18 h. Et$_3$N distilled from CaH$_2$ raised conversion to 80%.

TABLE 1

Pinacolborylation of Methyl 4-Bromobenzoate

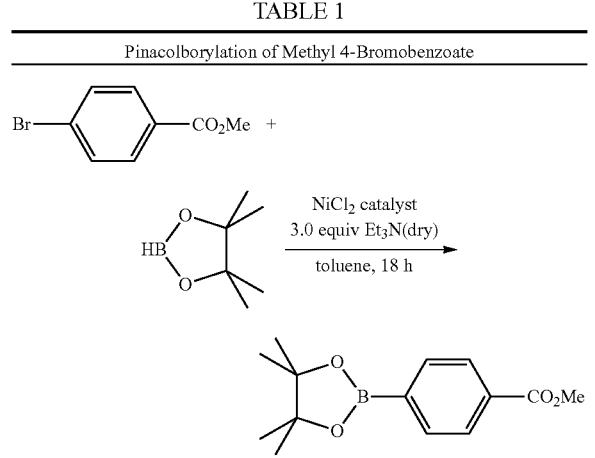

TABLE 1-continued

| HBpin (equiv) | catalyst (equiv) | temp (°C.) | conv. (%)[a] | byproduct (%)[a] |
|---|---|---|---|---|
| 2.0 | NiCl$_2$(dppp) (0.1) | 100 | 100 | 25 |
| 2.0 | NiCl$_2$(dppp) (0.1) | 80 | 0 | 0 |
| 2.0 | NiCl$_2$(dppp) (0.1) | 90 | 50 | 30 |
| 1.5 | NiCl$_2$(dppp) (0.1) | 100 | 80 | 35 |
| 2.0 | NiCl$_2$(dppp) (0.05) | 100 | 66 | 20 |
| 2.0 | NiCl$_2$(dppe) (0.1) | 100 | 90 | 10 |
| 2.0 | NiCl$_2$(PPh$_3$)$_2$ (0.2) | 100 | 70 | 15 |
| 2.0 | NiCl$_2$(dppp)/dppp (0.1) | 100 | 90 | 10 |

[a]Conversion and byproduct percentage determined via $^1$H NMR.

After conditions for 4-bromoanisole were optimized, effort was focused on reduction of apparent protiodeboration in methyl 4-bromobenzoate (Table 1). Methyl 4-bromobenzoate was obtained with 100% conversion after 18 h at 100° C. Decreased reaction temperature did not reduce the amount of protiodeboration but did have dramatic effects on conversion. Below 80° C. no measurable conversion was observed and at 90° C. the reaction proceeded to only 50% conversion in 18 h. As protiodeboration did not appear to be temperature dependent, the potential for catalyst or borane loading levels dependence was assessed. Reducing the catalyst from 10.0 mol % or the equiv of HBpin from 2.0 decreased conversion and failed to reduce protiodeboration. Catalyst effects were investigated. As determined previously (Morgan, et al, J. Appl. Polynl. Sci. 2000, 76, 1257) for bis- and tris-borylations, the most effective catalyst for mono-borylations is NiCl$_2$(dppp). This catalyst achieved 100% conversion of 4-carbonyl-methoxyphenyl-1-bromide in 18 h. NiCl$_2$(dppe) resulted in 90% conversion, while the conversion for NiCl$_2$(PPh$_3$)$_2$ was 70%. The NiCl$_2$(dppp) system can be tweaked to improve the product distribution. Introduction of an additional 1.0 equiv of dppp as a co-ligand reduced byproduct formation from 25% to 7%. It is unclear why dppp is superior to dppe or why increased dppp levels suppress protiodeboration. One possibility is that protiodeboration is catalyst mediated and that excess dppp shifts the equilibrium to the hypothetical Ni$^0$(dppp)$_2$ dormant species. The ligand effect is under experimental and computational investigations.

Optimized Ni-catalyzed pinacolborylation was tested on an electron withdrawing aryl bromide, two electron donating aryl bromides, and an aryl iodide yielding between 60-80% yield (Table 2). More substrates were tested, but they proved to be difficult to isolate. However, crude NMR generally showed good to excellent conversion for aryl bromides and aryl iodides but very limited conversion for aryl chlorides. The high conversions hinted at a promising reaction, but the frequent difficulties in purification of the pinacol boronate esters, the incompatibility of the purifiable pinacol boronate esters with NiCl$_2$(dppe) cross-coupling, and the generally sluggish hydrolysis to the boronic acid, instigated a search for alternatives to HBpin.

TABLE 2

Selected Ni-Catalyzed Pinacolborylations

| entry | substrate | product A | % yield[a] | ratio A:B[b] |
|---|---|---|---|---|
| 1 | Br—C6H4—CO2Me | Bpin—C6H4—CO2Me | 80 (100) | 13:1 |
| 2 | 4-Br-2-OMe-C6H3-OMe | Bpin-substituted dimethoxybenzene | 63 (96) | 10:1 |
| 3 | Br-trimethoxybenzene | Bpin-trimethoxybenzene | 79 (100) | 5:1 |
| 4 | I—C6H4—CH2CH2—CO2Me | Bpin—C6H4—CH2CH2—CO2Me | 60 (100)[c] | 5:1 |

[a] Isolated yield after column chromatography. $^1$H NMR conversions shown in parenthesis.
[b] Ratio based upon $^1$H NMR.
[c] Yield and conversion after 2 h.

While HBpin has been used frequently as a somewhat less expensive and easier to prepare replacement to bis(pinacolato)diboron, only a few other dialkoxyboranes have been explored (for example, Kennedy, et al., J. Organomet. Chem. 2.003, 680, 263 and Yang and Cheng, J. Am. Chem. Soc. 2001, 123(4), 761). A screen of inexpensive diols revealed that while many diols are incompatible with in situ generation of dialkoxyborane, neopentylglycol is well suited and has the added benefit of enforcing crystallinity. From $^1$H NMR, the reaction is believed to proceed via "in-situ" formed neopentylglycolborane, a compound that to our knowledge has not been reported in the literature, despite frequent use of its diboron analogue (Id.).

Due to the similarity of the pinacol and neopentylglycolborylations and good initial yields using previously optimized conditions, effort was not made to improve reaction conditions. However, due to the ease of neopentylglycol purification the effect of the quality of neopentylglycol and the catalyst and co-ligand effects conversion were assessed. Use of as received neopentylglycol resulted in 80% conversion, while its recrystallization from $CH_2Cl_2$ prior to use resulted in 100% conversion. As decreased HBpin loading level reduces conversion, this demonstrates that a minor drawback of the in situ generation is that we need to make certain that sufficient dialkoxyborane is available.

TABLE 3

Optimization of Neopentylglycolborylation

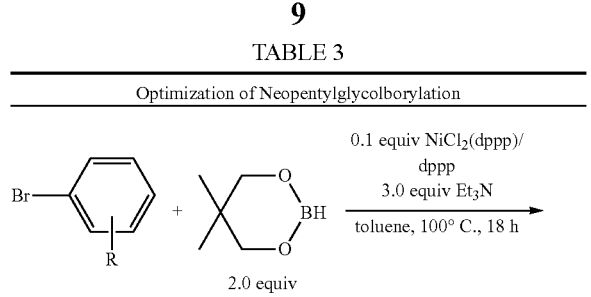

| R-group | diol quality | catalyst | conv. (%)[a] | byproduct (%)[a] |
|---|---|---|---|---|
| 3,5-OMe | As Rec. | NiCl$_2$(dppp) | 80 | nd |
| 3,5-OMe | Recrys. | NiCl$_2$(dppp)/dppp | 100 | nd |
| 3,5-OMe | Recrys. | NiCl$_2$(dppe) | 39 | nd |
| 4-CO$_2$Me | Recrys. | NiCl$_2$(dppp) | 92 | 17 |
| 4-CO$_2$Me | Recrys. | NiCl$_2$(dppp)/dppp | 95+ | 9.5 |

[a]Conversion and byproduct content determined by $^1$H NMR.

While NiCl$_2$(dppe) was only slightly less effective than NiCl$_2$(dppp) for pinacolborylations, it only showed 39% conversion for neopentylglycolborylation of an electron rich bromide. As expected, addition of co-ligand dppp did not reduce the overall conversion of an electron rich bromide. However, as in the case of pinacolborylations addition of dppp during neopentylglycolborylation of an electron poor substrate resulted in decreased protiodeboration (17% to 9.5%).

TABLE 4

Scope of Ni-Catalyzed Neopentylglycolborylation

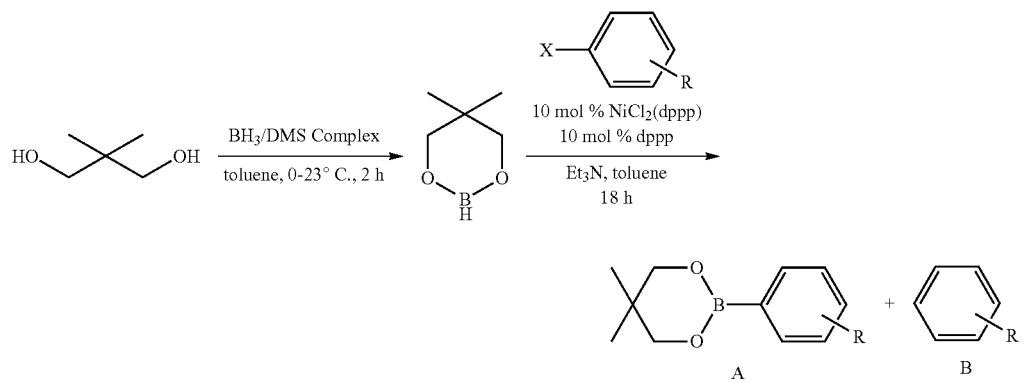

| entry | substrate | product A | % yield of A[a] | Ratio A:B[b] |
|---|---|---|---|---|
| 1 | Br—C$_6$H$_4$—CO$_2$Me | neopentylglycolboronate-C$_6$H$_4$-CO$_2$Me | 72[c] (100) | 9:1 |
| 2 | Br—C$_6$H$_4$—OMe | neopentylglycolboronate-C$_6$H$_4$-OMe | 78 (95) | 1:0 |
| 3 | 3,5-(OMe)$_2$-C$_6$H$_3$-Br | neopentylglycolboronate-3,5-(OMe)$_2$-C$_6$H$_3$ | 67 (95) | 6:1 |
| 4 | 2-Me-C$_6$H$_4$-Br | neopentylglycolboronate-2-Me-C$_6$H$_4$ | nd (100) | nd |

TABLE 4-continued

Scope of Ni-Catalyzed Neopentylglycolborylation

| entry | substrate | product A | % yield of A[a] | Ratio A:B[b] |
|---|---|---|---|---|
| 5 | Br-naphthyl | neopentylglycolboronate-naphthyl | 79 (100) | nd |
| 6 | I-C6H4-CH2CH2-CO2Me | neopentylglycolboronate-C6H4-CH2CH2-CO2Me | 72 (100)[d] | 6.7:1 |
| 7 | Cl-C6H4-CO2Me | neopentylglycolboronate-C6H4-CO2Me | nd (16) | nd |

[a]Yield after column chromotography.
[b]Yield and product ratio based on $^1$H NMR.
[c]Yield after MeOH recrystalization.
Conversion and yield after 2 h.

Using these optimized reaction conditions, neopentylglycolborylation was tested on a number of substrates (Table 4). This reaction works well with electron withdrawing and donating aryl bromides as well as aryl iodides (67-79% yield). The ortho-substituted bromide was not recovered by column chromatography, despite complete consumption of starting material. The aryl chloride proceeded to only 16% conversion under these reaction conditions.

While the aryl pinacolborates produced via NiCl$_2$(dppp) catalysis were not useful in NiCl$_2$(dppe) cross-coupling, fortuitously neopentylglycolboranes were more compliant. Of the aryl neopentylglycolboronate esters that we derived via NiCl$_2$(dppp)/dppp coupling, most did not participate in NiCl$_2$(dppe) Suzuki-Miyaura coupling using previously established conditions. However, methyl 4-(5,5-dimethyl-1,3,2-dioxaborinan-2-yl)benzoate (Table 4, entry 1) proceeded with very good to excellent yield in direct cross-coupling with aryl bromides and iodides and good yield with aryl chlorides (Table 5). Lack of reactivity of electron rich aryl neopentylglycolboronic esters was overcome by changing the base from K$_3$PO$_4$ to NaOH.

While not wanting to be bound by theory, three potential explanations arise for the base dependence on reactivity. (1) Electron rich neopentylglycolboronate esters do not form a strong enough borate complex with K$_3$PO$_4$ to allow transmetallation through an anionic pathway. (2) In situ hydrolysis of the boronate ester is essential for coupling using NiCl$_2$(dppe), and only strong bases like NaOH are able to hydrolyze the electron rich aryl neopentylglycolboronate ester. (3) NaOH induces a NiOH(dppe) pathway that enhance transmetallation for electron rich boronate esters (Braga, et al., J. Am. Chem. Soc. 2005, 127, 9298). The latter hypothesis is potentially discounted by the fact that refluxing 2-(3,5-dimethoxyphenyl)-5,5-dimethyl-1,3,2-dioxaborinane (Table 5, entry 3) with 3 equiv of NaOH in dioxane (i.e., reaction conditions without aryl halide and catalyst) only appears to mediate protiodeboration. It has been reported that Ni(COD)$_2$ catalyzes the cross-coupling of 5,5-dimethyl-2-phenyl-1,3,2-dioxaborinane with vinyl phosphates, using K$_3$PO$_4$ as base (Hansen, et al., Chem. Commun. 2006, 4136. It is therefore possible that the incompatibility of certain neopentylglycolboronate esters and all tested pinacolboronate esters with NiCl$_2$(dppe) cross-coupling relates to the inability to reduce the Ni$^{II}$Cl$_2$(dppe) pre-catalyst to active Ni catalyst.

Beyond the improvement of the synthesis of biaryls and related dendritic architectures (Percec, et al., J. Am. Chem. Soc. 2007, 129, 11265), this technique provides rapid access to analogues of expensive, but broadly useful, boronic acids. For example, 4-methoxycarbonylphenyl-1-boronic acid is used for the preparation of enantiomeric α-aminoketones (Yang, et al., J. Am. Chem. Soc. 2007, 127, 1132), but it is very expensive. Methods described in this paper achieve the pinacol- and neopentylboronate ester analogues in 80% and 72% yield respectively, and at significantly lower cost. Pinacol boronate esters are compatible with Pd-catalyzed crosscross-coupling (Baudoin, et al, Synlett. 2003, 13, 1009), and the neopentylboronate ester is compatible with Ni-catalyzed cross-coupling and should proceed with Pd (Chaumeil, et al., Tetrahedron 2000, 56, 9655). Also, the neopentylglycolboronate ester can be converted in high yield to the potassium trifluoroborate via $KHF_2$ and allows entrance into cross-coupling with aryl halides. All three species can be converted under appropriate hydrolytic, oxidative or fluorophillic conditions to the boronic acid (Yuen, et al., Tetrahedron Lett. 2005, 46, 7899).

As shown herein, $NiCl_2(dppp)$ catalyzed neopentylglycolborylation has been developed as a facile and inexpensive route to boronic acid substitutes, which can be immediately applied in $NiCl_2(dppe)$ catalyzed cross-coupling with aryl halides or converted to other useful intermediates.

The following example are intended to be illustrative and not limiting in nature. They provide additional detail and support for the results discussed above.

TABLE 5

Cross-coupling of Aryl Neopentylglycolboronates

General reaction: Aryl neopentylglycolboronate + X–Ar–$R_2$ $\xrightarrow{\text{10 mol \% NiCl}_2\text{(dppe), 10 mol \% dppe, K}_3\text{PO}_4 \text{ or NaOH, dioxane, 110° C., 18 h}}$ biaryl product

| entry | boronate ester | aryl halide | product | Yield[a] |
|---|---|---|---|---|
| 1 | neopentylglycolboronate-C6H4-CO2Me | Br-C6H4-Me | MeO2C-C6H4-C6H4-Me | 85 (100) |
| 2 | neopentylglycolboronate-C6H4-CO2Me | Br-C6H3(OMe)2 (3,5) | MeO2C-C6H4-C6H3(OMe)2 | 83 (92) |
| 3 | neopentylglycolboronate-C6H4-CO2Me | Br-C6H4-CO2Me | MeO2C-C6H4-C6H4-CO2Me | 79 (75) |
| 4 | neopentylglycolboronate-C6H4-CO2Me | Cl-C6H4-CO2Me | MeO2C-C6H4-C6H4-CO2Me | 67 (66) |
| 6 | neopentylglycolboronate-C6H4-CO2Me | I-C6H4-OMe | MeO2C-C6H4-C6H4-OMe | 92 (100) |
| 7 | neopentylglycolboronate-C6H4-CO2Me | MsO-C6H4-OBn | MeO2C-C6H4-C6H4-OBn | 0 (0) |
| 8[b] | neopentylglycolboronate-C6H4-OMe | Br-C6H3(OMe)2 (3,5) | MeO-C6H4-C6H3(OMe)2 | 70 (100) |
| 9[b] | neopentylglycolboronate-C6H3(OMe)2 (3,5) | I-C6H4-OMe | MeO-C6H4-C6H3(OMe)2 | 91 (100) |

[a] Yield after chromatography, approximate $^1$H NMR consumption of aryl halide in parenthesis.
[b] NaOH required as base, all other reactions utilize $K_3PO_4$.

EXAMPLES

General Considerations.

All reactions were performed in oven dried round-bottom flasks or Schlenk tubes with rubber septa tops under an inert atmosphere of $N_2$. Commercially available air sensitive reagents and dialkoxyboranes generated in situ were transferred via syringe or stainless steel cannula. Organic solutions were concentrated by rotary evaporation under house vacuum. Silica Gel Chromatography (Flash Chromatography) was performed using the classic procedure (Still, et al., J. Org. Chem. 1978, 43, 2923), employing silica gel (60 Å pore size, 230-400 Mesh, 40-64 pm particle size, SiliCycle). Thin Layer Chromatography was carried out on pre-coated aluminum plates (silica gel with indicator; layer thickness 200 pm; particle size, 2-25 pm; pore size 60 Å, from SIGMA-Aldrich). TLC plates were visualized by exposure to ultraviolet light.

Materials. Borane dimethylsulfide complex, 3,5-dimethoxy-1-bromobenzene, 4-(benyzyloxy)phenol, 1-bromonapthalene, 4-iodoanisole, hydrocinnamic acid, potassium hydrogen fluoride, 1,3-bis(diphenylphosophino) propane, and 1,2-bis(diphenphosophino)ethane were used as received from Aldrich. 1,1'-bis(diphenylphosphino)ferrocene, 99%, 2-(dicyclohexylphosphino)biphenyl, 98% and $Ni(COD)_2$ were used as received from Strem Chemicals. 4-chlorotoluene and 4-bromoanisole were used as received from Lancaster. 4-Bromotoluene and 4-bromoanisole were used as received from Lancaster. (i-Pr)$_2$EtN, CsF and P(Cy)$_3$ were used as received from Aldrich. $NiCl_2.6H_2O$ and pinacol were used as received from Acros. $H_2SO_4$, $MgSO_4$, NaCl, acetone, $NaHCO_3$, dichloromethane, ethyl acetate, THF, hexanes, and methanol were all used as received from Fischer. $MgSO_4$, NaCl, $NaHCO_3$, dichloromethane, acetone, ethyl acetate, hexanes, and methanol were all used as received from Fischer. $K_3PO_4$ (tribasic) from Fischer was dried at 40° C. prior to use. Neopentylglycol from Acros was recrystallized from dichloromethane prior to use. Triphenylphosphine from Aldrich was recrystallized from hexanes prior to use. Dioxane (ACS Reagent grade) from Fischer was refluxed over sodium ketyl until the solution turned purple and was freshly distilled before use. Toluene and triethylamine (ACS reagent grade) from Fischer were distilled over $CaH_2$ and stored under nitrogen prior to use. Deuterated solvents were obtained from Cambridge Isotope Labs. Ni-based catalysts $NiCl_2$(dppp) (Van Hecke, G. R.; Horrocks, W. D. Inorg. Chem. 1966, 5(11), 1968), $NiCl_2$(dppe) (Booth, G.; Chatt, J. J. Chem. Soc. 1965, 3238), $NiCl_2$(dppf) (Rudie, A. W.; Lichtenberg, D. W; Katcher, M. L; Davison, A. Inorg. Chem. 1978, 17(10), 2859), $NiCl_2(PPh_3)_2$ (Barnett, K. W. J. Chem. Educ. 1974, 51(6), 422), $NiCl_2(Et_3N)_2$ (Ahuja, I. S.; Brown, D. H; Nuttall, R. H.; Sharp, D. W. A. J. Inorg. Nucl. Chem. 1965, 27, 1105), $NiCl_2$(bpy) (Broomhead, J. A.; Dwyer, F. P. Aust. J. Chem. 1961, 14, 250), and Pd catalyst $PdCl_2$(dppf) (Hayashi, T.; Konishi, M.; Kobori, Y.; Kamada, M.; Higuchi, T.; Hirotsu, K. J. Am. Chem. Soc. 1984, 106, 158) were synthesized according to the original procedures.

Instrumentation.

$^1$H NMR (500 MHz or 360 MHz) and $^{13}$C NMR (125 MHz) spectra were recorded on a Bruker DRX 500 or a Bruker DMX 360 instrument, using TMS as internal standard. Chemical shifts are reported relative to internal chloroform (607.26 for $^1$H, 6077.0 for $^{13}$C), benzene (6 7.16 for $^1$H and 6 128.39 for $^{13}$C) or DMSO (6 2.50 for $^1$H and 6 39.51 for $^{13}$C) standard solvent for NMR. For organoboron compounds, carbons adjacent to boron were not observed due to peak broadening from the boron quadrapole moments. Melting temperatures were recorded on a Thomas-Hoover Uni-Melt apparatus and were reported without correction. High resolution mass spectra of new compounds were obtained on an Autospec high resolution double focusing chemical ionization spectrometer.

High-resolution mass spectra of new compounds were obtained on an Autospec high resolution double focusing chemical ionization spectrometer. Agilent GC 6890 coupled with an FID detector gas chromatograph and column HP 19091J-413 (5%-phenyl)methylpolysiloxane 30 m Length 0.32 mm internal diameter was used to follow the reaction conversions and to assess purity of final compounds complementary to the NMR technique. The crude reaction mixtures were diluted with THF stabilized with BHT (3%), which was used as internal standard. Inert atmosphere for air sensitive reagents and reactions ($Ni(COD)_2$-catalized cross-coupling) was provided by Innovative Technology System 1, Glove Box.

LIST OF ABBREVIATIONS

BH3.DMS borane dimethylsulfide complex
CI chemical ionization
DCM dichlormethane
dppe 1,2-bis(diphenylphosphino)ethane
dppf 1,1'-bis(diphenylphosphino)ferrocene
dppp 1,3-bis(diphenylphosphino)propane
equiv equivalent
$Et_3N$ triethylamine
g gram
HRMS high resolution mass spectrometry
Hz hertz
J coupling constant
mg milligram
mL milliliter
mmol millimole
Mp melting point
m/z mass-to-charge ratio
nd not determined
$NiCl_2$(dppe) (1,2-bis(diphenylphosphino)ethane)nickel(II) chloride
$NiCl_2$(dppp) (1,3-bis(diphenylphosphino)propane)nickel(II) chloride
$Ni(COD)_2$ bis(1,5-cyclopentadiene)nickel(0)
ppm parts per million
$R_f$ retention factor
OTs tosylate
OMs mesylate Synthesis of Reagents $NiCl_2$(dppe), $NiCl_2$(dppp) and $NiCl_2(PPh_3)_2$. Catalysts were prepared by refluxing a methanolic solution of nickel(II) dichloride hexahydrate with stoichiometric phopshine ligand according to literature procedures (Booth and Chatt, J. Chem. Soc. 1965, 3238). Analytical data agreed with those reported in the literature.

Synthesis of 4-(Benzyloxy)phenyl methanesulfonate. This compound was prepared according to literature methods starting from 4-(benzyloxy)phenol (Percec, et al., J. Org. Chem. 2004, 69, 3447).

Synthesis of Methyl 4-Iodohydrocinnamate

4-Iodohydrocinnamic acid was prepared from hydrocinnamic acid according to literature procedures using $H_5IO_6I_2$ (Kawasaki, et al., Tetrahedron Asymm. 2001, 12(4), 585). To a stirring solution of 4-iodohydrocinnamic acid (12.248, 44.4 mmol, 1.0 equiv) in methanol (75 mL), was added $H_2SO_4$ (2.2 mL). A reflux condenser was attached and the reaction mixture was heated to reflux at 75° C. for 15 h under $N_2$. The reaction mixture was cooled to 23° C. and the methanol was removed by rotary evaporation. The crude oil concentrate was diluted with DCM (100 mL) and ethyl acetate (15 mL). The solution was washed with water (100 mL), saturated aqueous sodium bicarbonate (100 mL) and saturated aqueous sodium chloride (100 mL). The organic layer was dried over anhydrous magnesium sulfate. The dried organics were filtered and concentrated to furnish methyl 4-iodohydrocinnamte as an off-white solid (12.898, 99%). Mp: 46° C.

In Situ Preparation of Neopentylglycolborane PBnpt) and Pinacolborane (5,5-Dimethyl-1,3,2-dioxaborinane and 4,4,5,5-tetramethyl-1,3,2-dioxaborolane) (HBpin)

To a stirring solution of neopentylglycol or pinacol (10.0 mmol, 2.0 equiv) in toluene (5 mL) at 0° C. was added $BH_3$-DMS (10.0 mmol, 2.0 equiv) dropwise via syringe under nitrogen. The reaction mixture was allowed to stir for 30 min at 0° C. and 90 min at 23° C. at which point gas evolution ceased. Neopentylglycolborane and pinacolborane were used directly in toluene solution without further purification or analysis.

Pinacolborane (HBpin) has been previously isolated and characterized (Tucker, et al., J. Org. Chem. 1992, 57, 3482). To our knowledge neopentylglycolborane (HBnpt) has not been isolated, used, or characterized. While isolation and purification of HBnpt was not attempted, formation of HBnpt was observed in situ by NMR analysis. Transferring a small aliquot of its toluene solution to a $N_2$ flushed NMR tube filled with benzene-$d^6$ via a J Young valve $^1$H-NMR and $^{13}$C-NMR spectra were collected. The NMR spectra confirmed the identity of the compounds.

General Procedure for the Synthesis of Aryl Neopentylglycol- and Pinacolboronic Esters.

A round-bottom flask was charged with an aryl halide (5.0 mmol, 1.0 equiv), $NiCl_2$(dppp) (0.5 mmol, 0.1 equiv), dppp (0.5 mmol, 0.1 equiv), and a Teflon® coated stirbar. The reaction vessel was evacuated for 10 min under high vacuum and backfilled with $N_2$. This process was repeated twice more. Toluene (5 mL) and $Et_3N$ (15.0 mmol, 3.0 equiv) were added. To the crimson-colored suspension was added freshly prepared neopentylglycolborane or pinacolborane (10.0 mmol, 2.0 equiv in 5 ml toluene) via cannula at 23° C. The reaction mixture was refluxed at 100° C. for 18 h. Upon completion, the reaction mixture was quenched via slow addition of saturated aqueous ammonium chloride (10 mL). The quenched reaction mixture was then diluted with ethyl acetate (10 mL) and washed with saturated aqueous ammonium chloride (3×50 mL). The aqueous layers were back-extracted with ethyl acetate (2×50 mL) and DCM (2×50 mL). The organic layers were combined, dried over anhydrous $MgSO_4$, filtered, and concentrated to achieve the crude product. Purification was achieved via silica gel chromatography or recrystallization.

Methyl 4-(4,4,5,5-tetramethyl-1,3,2-dioxaborolan-2-yl)benzoate

The crude product was made by the above procedure and purified by silica gel chromatography (DCM, $R_f$=0.53) to yield the product as white crystals (1.05 g, 80%). Mp=79-80.5° C. $^1$H and $^{13}$C NMR spectra agreed with those of the literature (Ishiyama, et al., J. Org. Chem. 1995, 60, 7508-7510).

2-(3,4-Dimethoxyphenyl)-4,4,5,5-tetramethyl-1,3,2-dioxaborolane

The crude product was made according the procedure above and purified by silica gel chromatography (10 hexanes: 1 ethyl acetate, $R_f$=0.16) to yield the product as white crystals (0.84 g, 63%). Mp=82-83° C. $^1$H and $^{13}$C NMR spectra agreed with those of the literature (Anastasi and Hartwig, J. Am. Chem. Soc. 2002, 124, 390).

4,4,5,5-Tetramethyl-2-(3,4,5-trimethoxyphenyl)-1,3,2-dioxaborolane

The crude product was made according the procedure above and purified by silica gel chromatography (10 hexanes: 1 ethyl acetate, $R_f$=0.13) to yield the product as white crystals (1.15 g, 79%). Mp=100-101.5° C. $^1$H and $^{13}$C NMR spectra were consistent with the expected product.

Methyl 3-[4-(4,4,5,5-tetramethyl-[1,3,2]dioxaborolan-2-yl)phenyl]propanoate

The crude product was made according the procedure above and purified via silica gel chromatography (3 DCM: 1 hexanes, $R_f$=0.21) to yield the product as white crystals (0.89 g, 60%). Mp=57-58° C. $^1$H and $^{13}$C NMR spectra agreed with those of the literature (Zaidlewicz and Wolan, J. Organomet. Chem. 2002, 657, 129). HRMS was consistent with the expected product.

Methyl 4-(5,5-dimethyl-1,3,2-dioxaborinan-2-yl)benzoate

This synthesis was performed on 3× scale (15.0 mmol of aryl halide) according to the procedure below. The crude product was recrystallized in methanol to yield the product as white crystals (2.68 g, 72%). Mp=113-114° C. $^1$H and $^{13}$C NMR spectra agreed with those of the literature (Ukai, et al., J. Am. Chem. Soc. 2006, 128(27), 8706). HRMS was consistent with the expected product.

2-(4-Methoxyphenyl)-5,5-dimethyl-1,3,2-dioxaborinane

The crude product was made according the procedure above and purified by silica gel chromatography (15 hexanes: 1 ethyl acetate, $R_f$=0.21) to yield the product as white crystals (0.86 g, 78%). Mp=57-58° C. $^1$H and $^{13}$C NMR spectra and HRMS were consistent with the expected product.

2-(3,5-Dimethoxyphenyl)-5,5-dimethyl-1,3,2-dioxaborinane

The crude product was made according the procedure above and purified by silica gel chromatography (10 hexanes: 1 ethyl acetate, $R_f$=0.28) to yield the product as white crystals (0.88 g, 67%). Mp=114-115° C. $^1$H and $^{13}$C NMR spectra and HRMS were consistent with the expected product.

5,5-Dimethyl-2-(naphthalen-1-yl)-1,3,2-dioxaborinane

The crude product was made according the procedure above and purified by silica gel chromatography (15 hexanes: 1 ethyl acetate, $R_f$=0.34) to yield the product as white crystals (0.95 g, 79%). Mp=69-70° C. $^1$H and $^{13}$C NMR spectra agreed with those of the literature (Ukai, et al., J. Am. Chem. Soc. 2006, 128(27), 8706). HRMS was consistent with the expected product.

Methyl 3-(4-(5,5-dimethyl-1,3,2-dioxaborinan-2-yl) phenyl)propanoate

The crude product was made according the procedure above and purified by silica gel chromatography (5 hexanes: 1 ethyl acetate, $R_f$=0.28) to yield the product as white crystals (1.00 g, 72%). Mp=68-69° C. $^1$H and $^{13}$C NMR spectra agreed with those of the literature (Ukai, et al., J. Am. Chem. Soc. 2006, 128(27), 8706). HRMS was consistent with the expected product.
General Procedure for Cross-Coupling of Neopentylglycolboronic esters and Aryl Halides A Schlenk tube was charged with aryl halide (0.67 mmol, 1.0 equiv), aryl boronic ester (0.81 mmol, 1.2 equiv), potassium phosphate or sodium hydroxide (2.02 mmol, 3.0 equiv), 1,2-bis(diphenylphosphino)ethane nickel(II) chloride (0.07 mmol, 0.1 equiv), 1,2-bis(diphenylphosphino)ethane (0.07 mmol, 0.1 equiv), and a Teflon coated stirbar. A reflux condenser was attached and the reaction mixture was evacuated for ten minutes under high vacuum. The vessel was backfilled with nitrogen. This process was repeated twice more. Dry dioxane was added via the T-neck and the reaction mixture was heated to 110° C. for 18 h. Near or upon reaching 110° C. the reaction color should change from red to yellow. The reaction mixture was cooled to room temperature and diluted with DCM (10 mL). The solution was filtered and the filtrated washed with DCM (100 mL). The filtrate was concentrated and purified via silica gel chromatography.

Dimethyl Biphenyl-4'4'-dicarboxylate

The crude product was made according the procedure above and purified via silica gel chromatography (5 hexanes: 1 ethyl acetate gradient to 1 hexanes: 1 Ethyl Acetate, $R_f$=0.40) gave desired product as white crystals. Yield from aryl chloride (0.15 g, 67%). Yield from aryl bromide (0.17 g, 79%). Mp: 212-213° C. $^1$H and $^{13}$C NMR spectra agreed with those of the literature (Kuroboshi, et al., J. Org. Chem. 2002, 68, 3938; Hennings, et al., Org. Lett. 1999, 1(8), 1205).

Methyl 4'-Methylbiphenyl-4-carboxylate

The crude product was made according the procedure above and purified via silica gel chromatography (5 hexanes: 1 ethyl acetate, $R_f$=0.52). Yield (0.13 g, 86%) as white crystals. Mp: 115-116° C. $^1$H and $^{13}$C NMR spectra agreed with those of the literature (So, et al., Org. Lett. 2007, 9, 2795.

Methyl 4'-methoxybiphenyl-4-carboxylate

The crude product was made according the procedure above and purified via silica gel chromatography (5 hexanes: 1 Ethyl Acetate, $R_f$=0.37). Yield (150 mg, 92%) as white crystals. Mp=173-174° C. $^1$H and $^{13}$C NMR spectra agreed with those of the literature (Miao and Chan, Org. Lett. 2003, 5, 5003; Zhang, J. Org. Chem. 2003, 68, 3729).

Methyl 3',5'-dimethoxybiphenyl-4-carboxylate

The crude product was made according the procedure above and purified by silica gel chromatography (5 hexanes:1 ethyl acetate gradient to 1 hexanes:1 ethyl acetate, $R_f$=0.68). Yield (0.15 g, 83%) as a white crystals. Mp=79-80° C. $^1$H and $^{13}$C NMR spectra agreed with those of the literature (Percec, et al., Chem. Eur. J. 2006, 12, 6216).

3,4',5-Trimethoxybiphenyl

The crude product was made according the procedure above and purified by silica gel chromatography (5 hexanes: 1 ethyl acetate gradient to 3 hexanes: 1 ethyl acetate, $R_f$=0.8). Yield from 3,5-dimethoxy-1-bromobenzene (0.13 g, 70%) as a white crystalline solid. Yield from 4-iodoanisole (0.15 g, 92%) as white crystals. Mp: 59° C. $^1$H and $^{13}$C NMR spectra agreed with those of the literature (Ackermann and Althammer, Org. Lett. 2006, 8, 3457).

Synthesis of Potassium Trifluoro(4-(methoxycarbonyl)phenyl)borate

To a stirring solution of methyl 4-(5,5-dimethyl-1,3,2-dioxaborinan-2-yl)benzoate (1.6 mmol, 1.0 equiv) in THF was added an aqueous solution of KHF$_2$ (8.9 mmol, 5.0 equiv in 3 mL). The solution was allowed to stir for 1 h. The reaction mixture was concentrated and the crude product was recrystallized from acetone to yield the desired product as white crystalline shards. (0.33 g, 87%). $^1$H and $^{13}$C NMR spectra and HRMS were consistent with the expected product.
Limited Intermediate Isolation Methodology
Synthesis All reactions were performed in oven dried two neck round-bottom flasks or Schlenk tubes with rubber septa tops under an inert atmosphere of N$_2$. Commercially available air sensitive reagents and dialkoxyboranes generated in situ were transferred via syringe. Silica Gel Chromatography (Flash Chromatography) was performed using silica gel (60 Å pore size, 230-400 Mesh, 40-64 μm particle size, SiliCycle). Thin Layer Chromatography was carried out on pre-coated aluminum plates (silicagel with F254 indicator; layer thickness 200 μm; particle size, 2-25 μm; pore size 60 Å, from SIGMA-Aldrich).
Fresh Preparation of Neopentylglycolborane To a cooled solution of neopentylglycol (10.0 mmol, 2.0 equiv) dissolved in toluene (5 mL) and maintained at 0° C. was slowly added BH3.DMS (10.0 mmol, 2.0 equiv) via syringe under nitrogen. After 30 min of stirring at 0° C., the reaction mixture was allowed to warm to rt and left stirring at rt until the gas evolution ceased (60-90 min). Neopentylglycolborane was used directly without further purification.
Sequential Neopentylglycolborylation A round-bottom flask charged with the aryl halide (5.0 mmol, 1.0 equiv), Ni (For exact amount of catalyst and co-ligand see Table 8; 10% loading was used for Ni catalysts not specified in Table 8). (NiCl$_2$(L)$_x$, Ni(COD)$_2$) or Pd (No co-ligand was used for Pd catalyst) catalysts (PdCl$_2$(dppf)) (0.5 mmol, 0.1 to 0.02 equiv), ligand (L: dppp, dppe, dppf, PPh$_3$, Et$_3$N, bpy, PCy$_3$) (0.5 mmol, 0.1 equiv), and a Teflon® coated stir bar was evacuated three times for 10 min under high vacuum and backfilled with N$_2$. Toluene (5 mL) and base (Et$_3$N or (i-Pr)$_2$EtN (15.0 mmol, 3.0 equiv) were added to the reaction mixture at rt. Freshly prepared neopentylglycolborane (10.0 mmol, 2.0 equiv in 5 ml toluene) was added to the red colored suspension via syringe at 23° C. The reaction mixture was heated to 100° C. and the conversion was followed by GC. After 2 h-12 h (reaction time depends on the type of the aryl halide; iodo derivatives were found to react faster, in 2-4 h, while bromo derivatives in 8-12 h), the reaction mixture was quenched via slow addition of saturated aqueous ammonium chloride (10 mL). The quenched reaction mixture was three times washed with saturated aqueous ammonium chloride and extracted with ethyl acetate (50 mL). The combined organic layers were dried over anhydrous MgSO₄, filtered, and concentrated. The crude product was purified by silica gel chromatography or recrystallization.

General Procedure for Two-Step One-Pot Neopentylglycolborylation

To a round-bottom flask, aryl halide (5.0 mmol, 1.0 equiv), neopentylglycol (10.0 mmol, 2.0 equiv), Ni catalyst (NiCl₂(dppp) or NiCl₂(dppe) (0.5 mmol, 0.1 equiv), ligand (L: dppp or dppe) (0.5 mmol, 0.1 equiv), and Teflon® coated stir bar was added. The flask was evacuated three times for 10 min under high vacuum and backfilled with N₂. Freshly distilled toluene was added under nitrogen via syringe and the reaction flask was then cooled to 0° C. BH3.DMS complex (10.0 mmol, 2.0 equiv) was added slowly under N₂ to the suspension. After 30 min of stirring at 0° C., the reaction mixture was allowed to warm to rt and left stirring for 1 h when the gas evolution ceased. Et₃N (15.0 mmol, 3.0 equiv) was added at rt and the reaction mixture was than heated to 100° C. After complete conversion (GC) the reaction was quenched with saturated solution of NH₄Cl and extracted with ethyl acetate. The combined organic layers were dried over anhydrous MgSO₄, filtered, and concentrated. The crude product was purified by silica gel chromatography or recrystallization.

General Procedure for Ni(COD)-2-Catalyzed Cross-Coupling of Neopentylglycolboronate Esters and Aryl Chlorides, Mesylates and Tosylates In a glove box with N₂ atmosphere, a Schlenk tube was charged with aryl halide, tosylate or mesylate (1.0 equiv), aryl neopentylglycolboronate (1.5 equiv), potassium phosphate (0.9 mmol, 3.0 equiv), Ni(COD)₂ (0.018 mmol, 0.06 equiv), tricyclohexylphosphine (0.11 mmol, 0.18 equiv), and a Teflon coated stirbar. Dry THF (2 ml) was added and reaction was left stirring for 8 h at rt. The reaction mixture was diluted with DCM (10 mL) and filtered. The filtrated solid was washed with DCM (100 mL) and the organic solvent concentrated. The coupling products were precipitated in MeOH and the white crystals were filtrated and washed with cold MeOH.

General Procedure for Pd-Catalyzed Cross-Coupling of Neopentylglycolboronate Esters and Aryl Halides A Schlenk tube was charged with aryl halide (0.67 mmol, 1.0 equiv), aryl boronate ester (0.81 mmol, 1.2 equiv), potassium phosphate or CsF (3.0 equiv), Pd catalyst (0.1 equiv), 2-(dicyclohexylphosphino)biphenyl (0.2 equiv) (co-ligand was used in the presence of Pd(OAc)₂ as catalyst and CsF as base (see Table 8, entries 13-15); reaction was performed at rt) and a Teflon coated stirbar. The reaction mixture was evacuated three times for ten minutes under high vacuum and backfilled with N₂. Dry dioxane was added via the T-neck and the reaction mixture was heated to 110° C. for 18 h. The reaction mixture was cooled to room temperature and diluted with DCM (10 mL). The solution was filtered and the filtrated washed with DCM (100 mL). The filtrate was concentrated and purified by silica gel chromatography.

General Procedure for Three-step One-Pot Neopentylglycolborylation and Cross-Coupling The same conditions for one-pot borylations are used. After complete conversion (determined by GC) the solvent is removed under vacuum and the PdCl₂(dppf) catalyst (0.1 eq), aryl halide, and base are added. The reaction vessel is evacuated three times for 15 min and backfilled with N₂. Dry dioxane is added and the reaction mixture is heated to 110° C. After 18 h the flask is cooled to rt and the salt is filtrated and washed 5 times with DCM. The organic solvent is concentrated and the compound is purified by column chromatography.

Neopentylglycolboronate esters of methyl 4-iodohydrocinnamate, 4-iodoanisole, 4-bromomethylbenzoate, dimethyl biphenyl-4,4'-dicarboxylate, methyl 4'-methylbiphenyl-4-carboxylate, methyl 4'-mehoxybiphenyl-4-carboxylate (Rosen, B.; Huang, C.; Percec, V. Org. Lett. 2008, 10, 2597) and cross-coupling products of methyl 4-(5,5-dimethyl-1,3, 2-dioxaborinan-2-yl)benzoate with 1-bromonaphthalene (Blettner, C. G.; König, W. A.; Stenzel, W.; Schotten, T. J. Org. Chem. 1998, 64, 3885) and 2-bromotoluene (Okamoto, K.; Akiyama, R.; Kobayashi, S. Org. Lett. 2004, 6, 1987) have been reported. The NMR spectra (Zhen, -Y. T; Qiao, —S. H. J. Am. Chem. Soc. 2004, 126, 3058) and mesylates (Percec, V.; Bae, J.-Y.; Zhao, M.; Hill, D. H. J. Org. Chem. 1995, 60, 176) have been synthesized in accordance with the literature procedures. The NMR spectra of these compounds agree with those reported in the literature. Only the synthesis and characterization by NMR of new compounds is presented in this manuscript.

Methyl 3-(4'-methoxybiphenyl-4-yl)propanoate

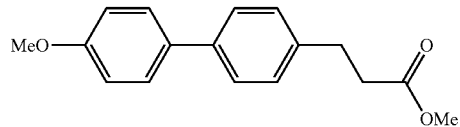 [SMILES: COC(=O)CCc1ccc(-c2ccc(OC)cc2)cc1]

The crude product was passed through a short silica gel column with (DCM) and recrystalyzed from MeOH to yield the product as white crystals (93% yield); mp 115° C. ¹H NMR (Acetone-d⁶, δ, ppm TMS): 2.66 (t, 2H, J=7.70 Hz, Ar—CH₂ 1 position), 2.95 (t, 2H, J=7.70 Hz, CH₂COO), 3.63 (s, 3H, COOMe, Ar 4 position), 3.94 (s, 3H, OMe, Ar 3 position), 7.01 (d, 2H, J=8.80 Hz, Ar 2',6' positions) 7.30 (d, 2H, J=8.25 Hz, Ar 2,6 positions), 7.52 (d, 2H, J=8.25 Hz, Ar 3,5 positions), 7.57 (d, 2H, J=8.80 Hz, Ar 3'5' positions); ¹³C NMR (Acetone-d⁶, δ, ppm TMS): 31.94, 36.86, 52.38, 56.43, 115.95, 128.11, 129.41, 130.45, 134.97, 140.23, 141.01, 160.94, 174.14; HRMS (CI) calcd. For C₁₇H₁₈O₃ (M⁺): 270.1256; Found: 270.1238.

4.7. Methyl 3-(3',4'-dimethoxybiphenyl-4-yl)propanoate

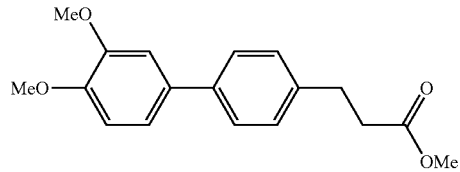 [SMILES: COC(=O)CCc1ccc(-c2ccc(OC)c(OC)c2)cc1]

The crude product was purified by silica gel chromatography (hexane:ethyl acetate 4:1), and recrystalyzed from MeOH to yield the product as white crystals (92% yield); mp 75° C. ¹H NMR (CDCl₃, δ, ppm TMS): 2.66 (t, 2H, J=7.70 Hz, Ar—CH₂ 1 position), 2.98 (t, 2H, J=7.70 Hz, CH₂COO), 3.69 (s, 3H, COOMe), 3.92 (s, 3H, OMe), 3.94 (s, 3H, OMe), 6.94 (d, 1H, J=8.25 Hz, Ar 5' position), 7.09 (d, 1H, J=2.20 Hz, Ar 2' position), 7.13 (dd, 1H, J=8.25 Hz, J=2.20 Hz, Ar 6' position), 7.25 (d, 2H, Ar 2,6 positions), 7.48 (d, 2H, Ar 3,5 positions); ¹³C NMR (CDCl₃, δ, ppm TMS): 30.77, 35.87, 56.15, 56.24, 110.80, 111.90, 119.51, 127.17, 128.87,

Methyl 3-(3',4',5'-trimethoxybiphenyl-4-yl)propanoate

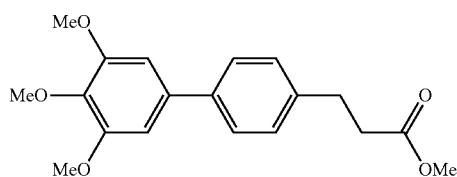 [SMILES: COC(=O)CCc1ccc(-c2cc(OC)c(OC)c(OC)c2)cc1]

The crude product was purified by silica gel chromatography (DCM) to yield the product as white crystals (93% yield); mp 73° C. $^1$H NMR (CDCl$_3$, δ, ppm TMS): 2.66 (t, 2H, J=7.70 Hz, Ar—CH$_2$ 1 position), 2.99 (t, 2H, J=7.70 Hz, CH$_2$COO), 3.69 (s, 3H, COOMe), 3.88 (s, 3H, Ar—OMe 4'-position), 3.91 (s, 6H, Ar—OMe 3',5' positions), 6.76 (s, 2H, Ar 2',6' positions), 7.25 (d, 2H, J=8.25 Hz, Ar 2,6 positions), 7.47 (d, 2H, J=8.25 Hz, Ar 3,5 positions); $^{13}$C NMR (CDCl$_3$, δ, ppm TMS): 31.34, 36.56, 52.23, 56.62, 99.42, 105.02, 115.87, 133.54 125.31, 129.26, 133.23, 161.71, 173.43; HRMS (CI) calcd. For C$_{19}$H$_{22}$O$_5$ (M$^+$): 330.1467; Found: 331.1551.

Methyl 3-(3',5'-dimethoxybiphenyl-4-yl)propanoate

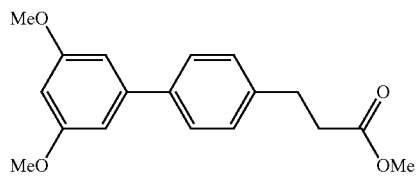 [SMILES: COC(=O)CCc1ccc(-c2cc(OC)cc(OC)c2)cc1]

The crude product was purified by silica gel chromatography (hexane:ethyl acetate 7:1) to yield the product as colorless oil (94% yield); mp 73° C. $^1$H NMR (CDCl$_3$, δ, ppm TMS): 2.66 (t, 2H, J=7.70 Hz, Ar—CH$_2$ 1 position), 2.98 (t, 2H, J=7.70 Hz, CH$_2$COO), 3.69 (s, 3H, COOMe), 3.84 (s, 6H, OMe), 3.94 (s, 3H, COOMe), 6.45 (t, 1H, J=2.20 Hz Ar 4' position), 6.71 (d, 2H, J=2.20 Hz, Ar 2',6' positions), 7.25 (d, 2H, J=8.25 Hz, Ar, 2,6 positions), 7.50 (d, 2H, J=8.25 Hz, Ar 3,5 positions). $^{13}$C NMR (CDCl$_3$, δ, ppm TMS): 30.62, 35.63, 51.62, 55.43, 99.31, 105.44, 127.32, 128.67, 139.31, 139.99, 143.26, 161.59, 173.28. LRMS (MALDI-TOF) calcd. For C$_{18}$H$_{20}$O$_4$ (M$^+$+H): 301.14; Found: 301.37.

The examples herein are the first examples of a three-steps one-pot methodology comprising two-steps one-pot in-situ preparation of neopentylglycolborane, followed by complementary Ni/Pd or Ni/Ni borylation and subsequent cross-coupling with aryl bromides, iodides, chlorides, mesylates, and tosylates. One-pot borylation and cross-coupling reactions require essentially quantitative conversion of aryl halide to boronate as residual aryl halide from the first step is a potential competitive coupling partner. To identify the most suitable catalysts for complete conversion several NiCl$_2$ complexes with dppp, dppe, PPh$_3$, dppf, Et$_3$N and bpy were screened. The catalytic activity toward aryl iodides, bromides and chlorides was investigated by systematic variation of the catalyst loading, reaction temperature, solvent and base. It was found that a decrease of the catalyst loading level from 10% to 5% and 2% for neopentylglycolborylation of aryl iodides did not affect the conversion. Instead a marked increase in the recovered yield was observed (Table 6, entries 1 and 2). Although aryl iodides are less atom efficient and synthetically accessible, they display enhanced reaction rates, achieving complete conversion in only 2 h. The less reactive aryl bromides required higher catalyst loading (5-10%) for complete consumption of the substrate. In some embodiments, screening the activity of different Ni-catalysts showed that NiCl$_2$(dppp) and NiCl$_2$(dppe) were the optimum catalysts in the borylation reactions with yields in the range of 78-98%. Table 6 summarizes the data. Lower yields were obtained in the case of NiCl$_2$(PPh$_3$)$_3$, NiCl$_2$, (dppf), NiCl$_2$(Et$_3$N)$_2$, NiCl$_2$(bpy)$_2$ and NiCl$_2$. Aryl iodides were found to be less sensitive to the Ni-catalyst/co-ligand employed, showing complete conversion with NiCl$_2$(dppe)/dppe. Aryl bromides resulted in mild but often noticeable decreases in conversion, when dppe replaced dppp as catalyst and anisole was used as solvent (Table 6 entries 8 vs 9, Table 7 entry 3). Because dppe is a less expensive ligand its interchangeability with dppp in the case of iodides is notable. In some cases, when toluene is used as solvent (Table 6 entries 6 and 10) dppe can be used with aryl bromides without diminished conversion. Ni(COD)$_2$ with PCy$_3$ co-ligand is known to be active toward the catalytic cross-coupling of aryl mesylates and tosylates. Application of this catalytic system to neopentylglycolborylation of an electron-rich aryl mesylate, however, resulted in low yield (Table 6 entry 13).

TABLE 6

Two-Steps Sequential Neopentylglycolborylation.

| entry | substrate | catalyst[a] (%) | solvent | conv[d]: yield[e] (%) |
|---|---|---|---|---|
| 1 | ![structure] | NiCl$_2$ (dppp) (5) | toluene | 100:86 |
| 2 | ![structure] | NiCl$_2$ (dppp) (2) | toluene | 100:95 |

TABLE 6-continued

Two-Steps Sequential Neopentylglycolborylation.

[Reaction scheme: X-C6H3(R) + neopentylglycolborane (5,5-dimethyl-1,3,2-dioxaborinane with BH), 0.1 equiv NiCl$_2$(Ligand)/Ligand, 3.0 equiv Et$_3$N or (i-Pr)$_2$EtN, 100° C., 18 h → aryl neopentylglycolboronate]

| entry | substrate | catalyst[a] (%) | solvent | conv[d]: yield[e] (%) |
|---|---|---|---|---|
| 3 | MeO–C6H4–I | NiCl$_2$(dppe) (10) | toluene | 100:98 |
| 4 | 4-(MeO$_2$C)C6H4–Br | NiCl$_2$(dppp) (10) | toluene | 100:81 |
| 5 | 4-(MeO$_2$C)C6H4–Br | NiCl$_2$(dppp) (10) | anisole | 94:89 |
| 6 | 4-(MeO$_2$C)C6H4–Br | NiCl$_2$(dppe) (10) | toluene | 100:90 |
| 7 | MeO–C6H4–Br | NiCl$_2$(dppp) (10) | toluene | 91:90 |
| 8 | MeO–C6H4–Br | NiCl$_2$(dppp) (10) | anisole | 100:94 |
| 9 | MeO–C6H4–Br | NiCl$_2$(dppe) (10) | anisole | 78:78 |
| 10[c] | 4-(MeO$_2$C)C6H4–Br | NiCl$_2$(dppe) (10) | toluene | 100:87 |
| 11[c] | MeO–C6H4–Br | NiCl$_2$(dppe) (10) | toluene | 93:83 |
| 12 | 4-(MeO$_2$C)C6H4–Cl | NiCl$_2$(dppp) (5) | toluene | 20:10 |
| 13 | MeO–C6H4–OMs | Ni(COD)$_2$[b] (6) | toluene | 16:8 |

[a]Co-ligand added in 1:1 ratio to catalyst.
[b]Co-ligand P(Cy)$_3$ 18%.
[c](i-Pr)$_2$NEt as base.
[d]Conversion determined by GC.
[e]Isolated yield.

Pinacolborylations using PdCl$_2$(dppf) and purified HBPin are known. See, Murata, M.; Watanabe, S.; Masuda, Y. J. Org. Chem. 1997, 62, 6458 and Billingsley, K. L.; Buchwald, S. L. J. Org. Chem. 2008, 73, 5589. However, the use of PdCl$_2$(dppf) in borylation with in-situ prepared neopentylglycolborane was ineffective, most probably due to Pd catalyst poisoning in the presence of excess DMS from the BH3.DMS complex.

One of the primary advantages rendered by transition metal-catalyzed borylations is tolerance to sensitive functional groups. See, Bronic Acids. Hall, D. G. Ed; Wiley-VCH: Weinheim, Germany, 2005. Triethylarnine is incompatible with many reagents bearing alkyl halides due to its nucleophilicity. N,N-Diisopropylethylamine (Hunig's base) is sterically hindered and exhibits reduced nucleophilicity. Pd-Catalyzed pinacolborylation in the presence of Hiinig's base was less effective than triethylamine. See, Murata, M.; Watanabe, S.; Masuda, Y. J. Org. Chem. 1997, 62, 6458 and Murata, M.; Oyama, T.; Watanabe, S.; Masuda, Y. J. Org. Chem. 2000, 65, 164. In Ni-catalyzed neopentylglycolborylation this was not the case (Table 6 entries 10 and 11). It has been proposed for Pd-catalyzed borylations that dialkoxyboranes work as a single entity with mine base. See, Murata, M.; Oyama, T.; Watanabe, S.; Masuda, Y. J. Org. Chem. 2000, 65, 164. This hypothesis may not hold in the case of Ni-catalyzed borylation as little decrease in conversion was observed despite the strong steric shielding of the diisopropyl groups in Hiinig's base.

Toluene and anisole were found to be effective solvents for Ni-catalyzed borylation. The more polar dioxane, although suitable for Ni-catalyzed Suzuki cross-coupling (Percec, V; Golding, G. M.; Smidrkal, J.; Weichold, O. J. Org. Chem. 2004, 69, 3447), and for Pd-catalyzed pinacolborylation (Murata, M.; Watanabe, S.; Masuda, Y. J. Org. Chem. 1997, 62, 6458 and Billingsley, K. L.; Buchwald, S. L. J. Org. Chem. 2008, 73, 5589) gave lower yields in neopentylglycolborylation (Table 6, entries 5, 8, and 9).

TABLE 7

Two-Steps One-Pot Neopentylglycolborylation

| entry | substrate | catalyst[a] (%) | solvent | conv[b]: yield[c] (%) |
|---|---|---|---|---|
| 1 | MeO-C6H4-I | $NiCl_2$(dppp) (10) | toluene | 100:95 |
| 2 | methyl 4-bromobenzoate | $NiCl_2$(dppp) (10) | dioxane | 95:63 |
| 3 | methyl 4-bromobenzoate | $NiCl_2$(dppp) (10) | anisole | 100:94 |
| 4 | methyl 4-bromobenzoate | $NiCl_2$(dppp) (10) | toluene | 100:98 |
| 5 | methyl 4-bromobenzoate | $NiCl_2$(dppe) (10) | toluene | 90:75 |

[a]Co-ligand added in 1:1 ratio to catalyst.
[b]Conversion determined by GC.
[c]Isolated yield.

Table 7 demonstrates that aryl neopentylglycolborane can be synthesized in a two-steps one-pot reaction. $BH_3$.DMS complex was slowly added to a suspension of the Ni-catalyst, co-ligand substrate, and neopentylglycol maintained at 0° C. After 1 hour (h) at room temperature (rt), the base was added and the reaction temperature was increased to 100° C. High yields for electron-rich and electron-deficient aryl iodides and bromides were obtained. $NiCl_2$(dppe)/dppe was also compatible with the two-steps one-pot procedure, but with lower conversion and yield (Table 6, entry 5).

Aryl mesylates and tosylates are inexpensive coupling partners with arylboronic acids and provide a desirable method of carbon-carbon bond formation starting from phenols.

In the only other reported use of Ni-catalysis with aryl neopentylglycolboronate esters, Ni(COD)$_2$/PPh$_3$ or PCy$_3$ was able to mediate cross-coupling of 5,5-dimethyl-2-phenyl-1,3,2-dioxaborinane with vinyl phosphates using $K_3PO_4$ as base. See, Hansen, A.; Ebran, J. P.; Gøgsig, T. M.; Skrystrup, T. Chem. Commun. 2006, 4136. The success achieved with Ni(COD)$_2$ suggested that the difficulties with $NiCl_2$(dppe) and $NiCl_2$(PCy$_3$), arose in the reduction of Ni(II) pre-catalysts to the active Ni(0) species. By switching to Ni(COD)$_2$PCy$_3$, these problems were eliminated (Table 8). At rt complete conversion was achieved with both electron deficient (entries 1 and 2) and electron-rich (entries 3, 4, and 5) aryl neopentylglycolboronate with both electron-rich and electron-deficient aryl mesylates and tosylates. Good yields were also obtained with aryl chlorides.

TABLE 8

Ni-Catalyzed Cross-Coupling of Chlorides, Mesylates, and Tosylates.

| entry | substrate | boronate ester | conv[a]:yield[b] |
|---|---|---|---|
| 1 | methyl 4-(tosyloxy)benzoate | methyl 4-(neopentylglycolboronate)benzoate | 100:93 |
| 2 | 4-methoxyphenyl mesylate | methyl 4-(neopentylglycolboronate)benzoate | 100:98 |
| 3 | 4-methoxyphenyl tosylate | 4-methoxyphenyl neopentylglycolboronate | 100:95 |
| 4 | methyl 4-(tosyloxy)benzoate | 4-methoxyphenyl neopentylglycolboronate | 100:91 |
| 5 | 4-methoxyphenyl mesylate | 4-methoxyphenyl neopentylglycolboronate | 100:94 |
| 6 | 4-chlorotoluene | 4-methoxyphenyl neopentylglycolboronate | 79:76 |

[a] Conversion determined by GC.
[b] Isolated yield.

Reaction conditions: Ni(COD)$_2$ (6%), P(Cy)$_3$ (18%), K$_3$PO$_4$, THF 25° C. 12 h.

Pd-Catalyzed cross-coupling also provides a complementary pathway to biaryls from aryl neopentylglycolboronate esters. PdCl$_2$(dppf) catalyzed cross-coupling was achieved with excellent conversion and yield with diverse aryl bromides/iodides including fused aromatics, ortho-substituted, electron-rich and electron deficient aryl neopentylglycolboronate ester (Table 9). Pd-catalyzed cross-coupling is tolerant to a wider array of catalysts and temperatures than Ni-catalyzed cross coupling. Aryl chlorides, (Table 9, entry 15) reached high conversion and yield through the use of a Buchwald ligand (Noefe, J. P.; Singer, R. A.; Yang, B. H.; Buchwald, S. L. J. Am. Chem. Soc. 1999, 121, 9550). Pd-catalyzed cross-coupling does not provide cost advantages or increased scope in comparison to Ni(COD)$_2$PCy$_3$. However, it does lead to a very simple synthetic method for three-steps one-pot procedure that includes in situ synthesis of neopentylglycolborane and cross-coupling (Table 10).

In this three steps one-pot procedure, the same conditions for the borylation as employed in the two-steps one-pot borylation procedure were used. However, at the completion of the reaction, the product was not isolated. Rather, the solvent was removed in a rotary evaporator and the crude solid redissolved in dioxane followed by addition of Pd-catalyst, ligand, aryl halide, and K$_3$PO$_4$. The cross coupling proceeds with good overall yield (Table 10).

In some aspects, the invention provides a versatile NiCl$_2$(dppp) and NiCl$_3$(dppe)-catalyzed neopentylglycolborylation of aryl iodides and bromides that proceeds at low catalyst loading, in toluene, anisole and dioxane in a two-steps one-pot procedure was developed. The cross-coupling step was compatible with both electron-rich and electron-deficient aryl neopentylglycolboronates in the presence of K$_3$PO$_4$ base. High yield Ni-catalyzed cross-coupling at rt of neopentylglycolboronates with aryl mesylates, tosylates and chlorides was obtained in the presence of Ni(COD)$_2$/PCy$_3$. Likewise, efficient Pd-catalyzed cross-coupling was elaborated for a broad array of aryl neopentylglycolboronates with aryl chlorides, bromides and iodides. This complementary approach gives rise to the rapid synthesis of biphenyls through a three-steps one-pot method and demonstrates the synthetic competitiveness of in situ prepared neopentylglycolborane versus that of tetra(alkoxy)diboron derivatives.

TABLE 9

Pd-Catalyzed Cross-Coupling of Aryl Halides.

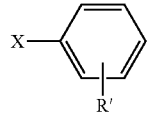

| entry | aryl halide | boronate ester | catalyst (%) | base | temp (° C.) | conv[b]: yield[c] (%) |
|---|---|---|---|---|---|---|
| 1 | MeO–C6H4–I | methyl 4-(5,5-dimethyl-1,3,2-dioxaborinan-2-yl)benzoate | PdCl$_2$(dppf) (10%) | K$_3$PO$_4$ | 80 | 100:90 |
| 2 | MeO–C6H4–I | MeO–C6H4–B(neopentylglycolate) | PdCl$_2$(dppf) (10%) | K$_3$PO$_4$ | 110 | 100:93 |
| 3 | MeO–C6H4–I | methyl 3-(4-(5,5-dimethyl-1,3,2-dioxaborinan-2-yl)phenyl)propanoate | PdCl$_2$(dppf) (10%) | K$_3$PO$_4$ | 110 | 100:90 |
| 4 | MeO–C6H4–Br | methyl 4-(5,5-dimethyl-1,3,2-dioxaborinan-2-yl)benzoate | PdCl$_2$(dppf) (2%) | K$_3$PO$_4$ | 110 | 100:95 |
| 5 | MeO–C6H4–Br | methyl 4-(5,5-dimethyl-1,3,2-dioxaborinan-2-yl)benzoate | Pd(OAc)$_2$ (10%) | K$_3$PO$_4$ | 110 | 95:82 |
| 6 | MeO–C6H4–Br | methyl 4-(5,5-dimethyl-1,3,2-dioxaborinan-2-yl)benzoate | PdCl$_2$ | K$_3$PO$_4$ | 110 | 100:81 |
| 7 | MeO–C6H4–Br | methyl 4-(5,5-dimethyl-1,3,2-dioxaborinan-2-yl)benzoate | PdCl$_2$(dppf) (10%) | CsF | 25 | 85:84 |
| 8 | MeO–C6H4–Br | methyl 4-(5,5-dimethyl-1,3,2-dioxaborinan-2-yl)benzoate | PdCl$_2$(dppf) (10%) | K$_3$PO$_4$ | 110 | 100:94 |
| 9 | methyl 4-bromobenzoate | MeO–C6H4–B(neopentylglycolate) | PdCl$_2$(dppf) (10%) | K$_3$PO$_4$ | 110 | 100:95 |

TABLE 9-continued

Pd-Catalyzed Cross-Coupling of Aryl Halides.

| entry | aryl halide | boronate ester | catalyst (%) | base | temp (° C.) | conv[b]: yield[c] (%) |
|---|---|---|---|---|---|---|
| 10 | 3,4,5-trimethoxybromobenzene | methyl 3-(4-(5,5-dimethyl-1,3,2-dioxaborinan-2-yl)phenyl)propanoate | PdCl$_2$(dppf) (10%) | K$_3$PO$_4$ | 110 | 100:93 |
| 11 | 3,4-dimethoxybromobenzene | methyl 3-(4-(5,5-dimethyl-1,3,2-dioxaborinan-2-yl)phenyl)propanoate | PdCl$_2$(dppf) (10%) | K$_3$PO$_4$ | 110 | 100:92 |
| 12 | 3,5-dimethoxybromobenzene | methyl 3-(4-(5,5-dimethyl-1,3,2-dioxaborinan-2-yl)phenyl)propanoate | PdCl$_2$(dppf) (10%) | K$_3$PO$_4$ | 110 | 100:94 |
| 13 | 1-bromonaphthalene | methyl 4-(5,5-dimethyl-1,3,2-dioxaborinan-2-yl)benzoate | Pd(OAc)$_2$[a] (10%) | CsF | 25 | 100:97 |
| 14 | 2-bromotoluene | methyl 4-(5,5-dimethyl-1,3,2-dioxaborinan-2-yl)benzoate | Pd(OAc)$_2$[a] (10%) | CsF | 25 | 100:99 |
| 15 | methyl 4-chlorobenzoate | methyl 4-(5,5-dimethyl-1,3,2-dioxaborinan-2-yl)benzoate | Pd(OAc)$_2$[a] (10%) | CsF | 25 | 100:99 |
| 16 | methyl 4-chlorobenzoate | methyl 4-(5,5-dimethyl-1,3,2-dioxaborinan-2-yl)benzoate | PdCl$_2$(dppf) (10%) | K$_3$PO$_4$ | 110 | 23:17 |

[a]Co-ligand 2-(dicyclohexylphosphino)biphenyl (20%).
[b]Conversion determined by GC.
[c]Isolated yield.

TABLE 10

One-Pot Borylation and Cross-Coupling of Neopentylglycolboronate Esters with Aryl Halides.

[Reaction scheme: methyl 4-bromobenzoate + neopentyl glycol (HOCH$_2$C(CH$_3$)$_2$CH$_2$OH), BH$_3$·DMS, 0.1 equiv NiCl$_2$(dppp)/dppp, 6.0 equiv Et$_3$N, Toluene; 1) 0 °C, 30 min, 0 °C–25 °C 90 min; 2) 100 °C, 18 h → neopentylglycol boronate ester of methyl benzoate; then + ArX (X, R), PdCl$_2$(dppf), K$_3$PO$_4$, 110 °C, Dioxane 18 h → biaryl methyl ester product]

| entry | aryl halide 1 | aryl halide 2 | Yield (%) |
|---|---|---|---|
| 1 | methyl 4-bromobenzoate | 4-bromoanisole (MeO-C$_6$H$_4$-Br) | i) 77[a] ii) 72[b] |
| 2 | methyl 4-bromobenzoate | methyl 4-bromobenzoate | i) 77[a] ii) 74[b] |

[a] Yield determined by GC.
[b] Overall isolated yield.

Additional results are presented in Tables 11 and 12.

TABLE 11

Two-Step Sequential Neopentylglycolborylation

[Reaction scheme: ArX (X, R) + neopentylglycolborane (1.2 equiv), 0.1 equiv NiCl$_2$(Ligand)/Ligand, 3.0 equiv Et$_3$N, 100 °C, 18 h → aryl neopentylglycolboronate]

| entry | substrate | catalyst[a] (%) | solvent | convn[b]: yield (%) |
|---|---|---|---|---|
| 1 | methyl 3-(4-iodophenyl)propanoate | NiCl$_2$(dppf) (5) | toluene | 94:37[d] |
| 2 | methyl 4-bromobenzoate | NiCl$_2$(dppp) (5) | toluene | 85:77 |
| 3 | methyl 4-bromobenzoate | NiCl$_2$(PPh$_3$)$_2$[e] (5) | toluene | 56:6 |
| 4 | methyl 4-bromobenzoate | NiCl$_2$(dppp) (10) | dioxane | 64:55 |
| 5 | methyl 4-bromobenzoate | PdCl$_2$(dppf)[f] (10) | toluene | 45:9 |

TABLE 11-continued

Two-Step Sequential Neopentylglycolborylation

ArX + neopentylglycolborane (1.2 equiv), 0.1 equiv NiCl₂(Ligand)/Ligand, 3.0 equiv Et₃N, 100° C., 18 h → Ar-B(neopentylglycolate)

| entry | substrate | catalyst[a] (%) | solvent | convn[b]: yield (%) |
|---|---|---|---|---|
| 6 | methyl 4-bromobenzoate | NiCl₂(dppe) (10) | anisole | 34:34 |
| 7 | methyl 4-bromobenzoate | NiCl₂(dppe) (10) | dioxane | 85:74 |
| 8 | methyl 4-bromobenzoate | NiCl₂(Et₃N)₂ | toluene | 15:0 |
| 9 | methyl 4-bromobenzoate | NiCl₂(bpy) | toluene | 37:13 |
| 10 | 4-bromoanisole | NiCl₂(dppp) (10) | dioxane | 48:48 |
| 11 | 4-bromoanisole | NiCl₂(dppe) (10) | dioxane | 39:39 |
| 12 | 4-bromo-1,2-dimethoxybenzene | NiCl₂(dppp)[e] (5) | toluene | 38:29 |
| 13 | 4-bromobenzonitrile | NiCl₂(dppe) (10) | toluene | 77:54 |
| 14 | 4-bromostyrene | NiCl₂(dppp) (5) | toluene | 20:10 |
| 15 | 2-bromotoluene | NiCl₂(dppe) (10) | toluene | 10:10 |
| 16 | 4-chloronitrobenzene | NiCl₂(dppe) (10) | toluene | 36:3 |
| 17 | methyl 4-chlorobenzoate | NiCl₂(dppf) (10) | toluene | 10:5 |

[a]Co-ligand added in 1:1 ratio to catalyst.
[b]Conversion determined by GC.
[c]GC yield.
[d]major dehalogenated byproduct.
[e]PPh₃ co-ligand 10%; reaction temperature 80° C.
[f]no co-ligand required.

TABLE 12

Pd-Catalyzed Cross-Coupling of Aryl Halides

| entry | aryl halide | boronate ester | catalyst (%) | base | temp (°C.) | convn[a]: yield[b] (%) |
|---|---|---|---|---|---|---|
| 1 | MeO–C6H4–Br | methyl 4-(5,5-dimethyl-1,3,2-dioxaborinan-2-yl)benzoate | PdCl2(dppf) (10%) | NEt3 | 80 | 50:0 |
| 2 | MeO–C6H4–Br | methyl 4-(5,5-dimethyl-1,3,2-dioxaborinan-2-yl)benzoate | PdCl2(dppf) (10%) | K3PO4 | 110 | 100:92 |
| 3 | MeO–C6H4–Br | methyl 4-(5,5-dimethyl-1,3,2-dioxaborinan-2-yl)benzoate | PdCl2(MeCN)2 (10%) | K3PO4 | 110 | 100:57 |
| 4 | MeO–C6H4–Br | methyl 4-(5,5-dimethyl-1,3,2-dioxaborinan-2-yl)benzoate | PdCl2(dppf) (2%) | K3PO4 | 25 | 53:46 |
| 5 | MeO–C6H4–Br | methyl 4-(5,5-dimethyl-1,3,2-dioxaborinan-2-yl)benzoate | PdCl2(dppf) (1%) | K3PO4 | 110 | 100:93 |
| 6 | MeO–C6H4–Br | methyl 4-(5,5-dimethyl-1,3,2-dioxaborinan-2-yl)benzoate | PdCl2 (10%) | K3PO4 | 110 | 100:81 |
| 7 | MeO–C6H4–Br | 2-(3,5-dimethoxyphenyl)-5,5-dimethyl-1,3,2-dioxaborinane | PdCl2(dppf) (10%) | K3PO4 | 110 | 92:79 |

[a]Conversion determined by GC.
[b]Isolated yield.

What is claimed:

1. A process for the synthesis of a compound of the formula:

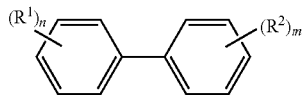

I wherein:
- $R^1$ and $R^2$ are each, independently, $C_1$-$C_{12}$ alkyl, $CO_2R^3$, $OR^4$, $R^5(OR^6)$, or $C_6$-$C_{18}$ aryl;
- $R^3$-$R^6$ are each, independently, $C_1$-$C_{12}$ alkyl or $C_6$-$C_{12}$ aryl; and
- n and m are each, independently, 0 or an integer from 1-5;

said process comprising:
reacting a compound of the formula HO—$R^7$—OH with $BH_3$ and a compound of the formula

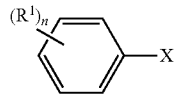

II in the presence of a nickel-containing catalyst to produce a first product, where $R^7$ is a $C_2$-$C_{12}$ hydrocarbon group and X is a halogen, OTs, or OMs;

contacting the first product with a compound of the formula:

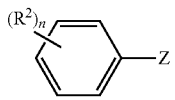

III in the presence of a nickel-containing catalyst to produce a compound of formula I, where Z is a halogen and where the nickel-containing catalyst is independently selected from $NiCl_2(dppp)$, $NiCl_2(dppe)$, $NiCl_2(PPh_3)_2$ and $Ni(COD)_2$.

2. A process for the synthesis of a compound of the formula:

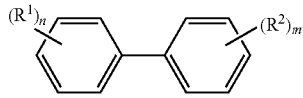

I wherein:
- $R^1$ and $R^2$ are each independently, $C_1$-$C_{12}$ alkyl, $CO_2R^3$, $OR^4$, $R^5(OR^6)$, or $C_6$-$C_{18}$ aryl;
- $R^3$-$R^6$ are each independently, $C_1$-$C_{12}$ alkyl or $C_6$-$C_{12}$ aryl; and
- n and m are each, independently, 0 or an integer from 1-5;

said process comprising:
reacting a compound of the formula HO—$R^7$—OH with $BH_3$ to produce an intermediate compound prior to contacting said intermediate compound with a compound of the formula:

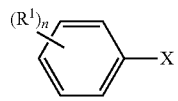

II in the presence of a nickel-containing catalyst to produce a first product, where $R^7$ is a $C_2$-$C_{12}$ hydrocarbon group and X is a halogen, OTs, or OMs;

contacting the first product with a compound of the formula:

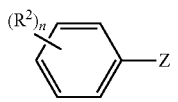

III in the presence of a nickel-containing catalyst to produce a compound of formula I, where Z is a halogen and where the nickel-containing catalyst is independently selected from $NiCl_2(dppp)$, $NiCl_2(dppe)$, $NiCl_2(PPh_3)_2$ and $Ni(COD)_2$.

3. The process of claim 1, wherein the nickel-containing catalyst is $NiCl_2(dppp)$.

4. The process of claim 1, wherein said compound of formula I is prepared in the presence of toluene solvent.

5. The process of claim 1, wherein n and m are each, independently, 1 or 2.

6. The process of claim 1, wherein at least one of $R^1$ and $R^2$ is $CO_2R^3$ where $R^3$ is methyl or ethyl.

7. The process of claim 1, wherein;
- $R^1$ and $R^2$ are each, independently, $C_1$-$C_4$ alkyl, $CO_2R^3$, $OR^4$, or $C_6$-$C_{18}$ aryl; and
- $R^3$-$R^6$ are each, independently, $C_1$-$C_4$ alkyl or $C_6$-$C_{12}$ aryl.

8. The process of claim 1, wherein X is Br.

9. The process of claim 1, wherein said first product is of the formula

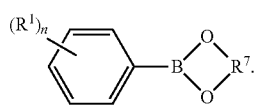

IV

10. The process of claim 1, wherein said reacting and contacting steps are performed seriatim.

11. The process of claim 10, wherein said reacting and contacting steps are performed seriatim in a single reaction vessel.

* * * * *